United States Patent [19]

Nakatsuka et al.

[11] Patent Number: 5,300,661
[45] Date of Patent: Apr. 5, 1994

[54] PROCESS FOR PREPARATION OF A RECORDING MATERIAL COMPRISING A NOVEL CRYSTAL OF A FLUORAN COMPOUND

[75] Inventors: Masakatsu Nakatsuka; Atsuo Otsuji; Kiyoharu Hasegawa; Kazuyoshi Kikkawa; Akihiro Yamaguchi, all of Kanagawa, Japan

[73] Assignee: Mitsui Toatsu Chemicals, Inc., Tokyo, Japan

[21] Appl. No.: 94,727

[22] Filed: Jul. 21, 1993

Related U.S. Application Data

[62] Division of Ser. No. 949,932, Sep. 24, 1992, which is a division of Ser. No. 717,568, Jun. 19, 1991, Pat. No. 5,185,453.

[30] Foreign Application Priority Data

Jun. 19, 1990 [JP] Japan .................................. 2-158763
Oct. 15, 1990 [JP] Japan .................................. 2-273401

[51] Int. Cl.$^5$ .......................................... C07D 311/88
[52] U.S. Cl. .................................................. 549/226
[58] Field of Search .......................................... 549/226

[56] References Cited

U.S. PATENT DOCUMENTS 5,185,453  2/1993  Nakatsuka et al. ................. 549/226

*Primary Examiner*—C. Warren Ivy
*Assistant Examiner*—A. Owens
*Attorney, Agent, or Firm*—Millen, White, Zelano, & Branigan

[57] ABSTRACT

Disclosed are novel crystal of the fluoran compound represented by the formula (I)

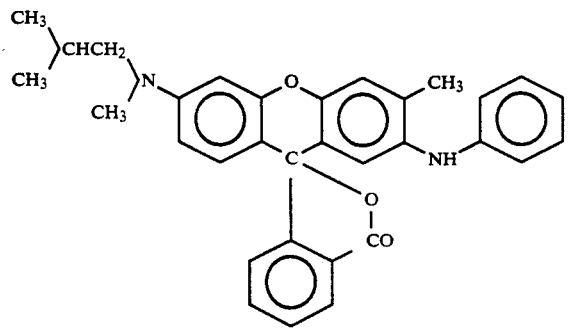

,characterized by a specific X-ray diffraction diagram; preparation process thereof; and recording materials comprising the crystal.

3 Claims, 1 Drawing Sheet

PROCESS FOR PREPARATION OF A RECORDING MATERIAL COMPRISING A NOVEL CRYSTAL OF A FLUORAN COMPOUND

This is a division of application Ser. No. 07/949,932 now allowed filed Sep. 24, 1992, which is a division of Ser. No. 07/717,568, filed Jun. 19, 1991 now U.S. Pat. No. 5,185,453.

BACKGROUND OF THE INVENTION

1) Field of the Invention

The present invention relates to a fluoran compound which is useful as a color forming compound in recording materials such as pressure sensitive and heat-sensitive recording materials. More particularly, the invention relates to crystal of the fluoran compound, to a process for the preparation of said crystal and to the recording materials comprising said crystal.

2) Description of the Prior Art

Pressure-sensitive recording, heat sensitive recording and electroheat-sensitive recording have conventionally been used as systems for recording transferred information through the mediation of external energy, such as pressure, heat or electricity, by utilizing a color reaction between a colorless or pale colored electron donative compound (color forming compound) and an organic or inorganic electron acceptor (developer).

In these recording systems, many fluoran compounds have widely been used as the color forming compound.

For example, 3-N-n-butyl-N methylamino-7-anilino-fluoran compound has been disclosed in Japanese Laid-Open Patent SHO 59-68373(1984).

The fluoran compound represented by the formula (I):

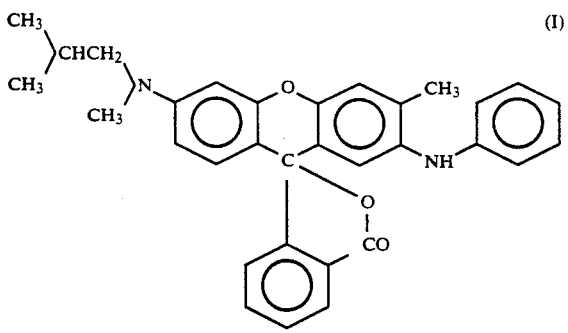

has been disclosed as a color developing compound in Japanese Laid-Open patent SHO 60-47066(1985) and described to have a melting point of 101° to 103° C.

When the compound is used as a color developing material for recording materials such as a heat-sensitive recording material and mixed with a developer such as bisphenol A, the compound itself colors dark gray and provides only a dark gray colored (soiled) paper by applying the compound to a paper. Further the compound has a disadvantage of poor storage-stability such as light resistance and leads to difficulty in practical use.

OBJECT OF THE INVENTION

An object of the present invention is to improve the disadvantages of the fluoran compound of the above formula (I) as a color forming agent of the recording materials and to provide crystalline form of the fluoran compound of the formula (I) having excellent properties for use in the pressure-sensitive and heat-sensitive recording materials, particularly in the heat-sensitive recording materials.

SUMMARY OF THE INVENTION

The present inventors have carried out an intensive investigation on the properties of the recording material, heat-sensitive recording material in particular, obtained by using the compound of the formula (I). As a result, they have found that a stable crystal having a melting point higher than the conventionally known melting point exists in the compound of the formula (I) and that the stable crystal has excellent properties as a color forming compound for use in the pressure-sensitive and heat-sensitive recording materials. They have also found a process for isolating the crystal and completed the invention.

One aspect of the present invention relates to a crystal of the fluoran compound represented by the formula (I):

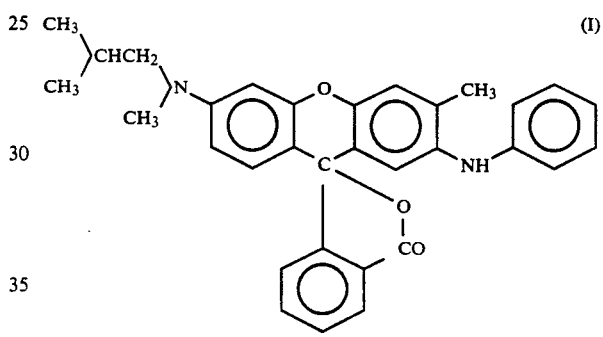

Another aspect of the invention relates to a process for preparing the crystal of the fluoran compound.

Further aspect of the invention relates to a recording material comprising the crystal.

The crystal of the fluoran compound of the formula (I) has excellent properties as a color forming compound of recording materials.

Figure 1:
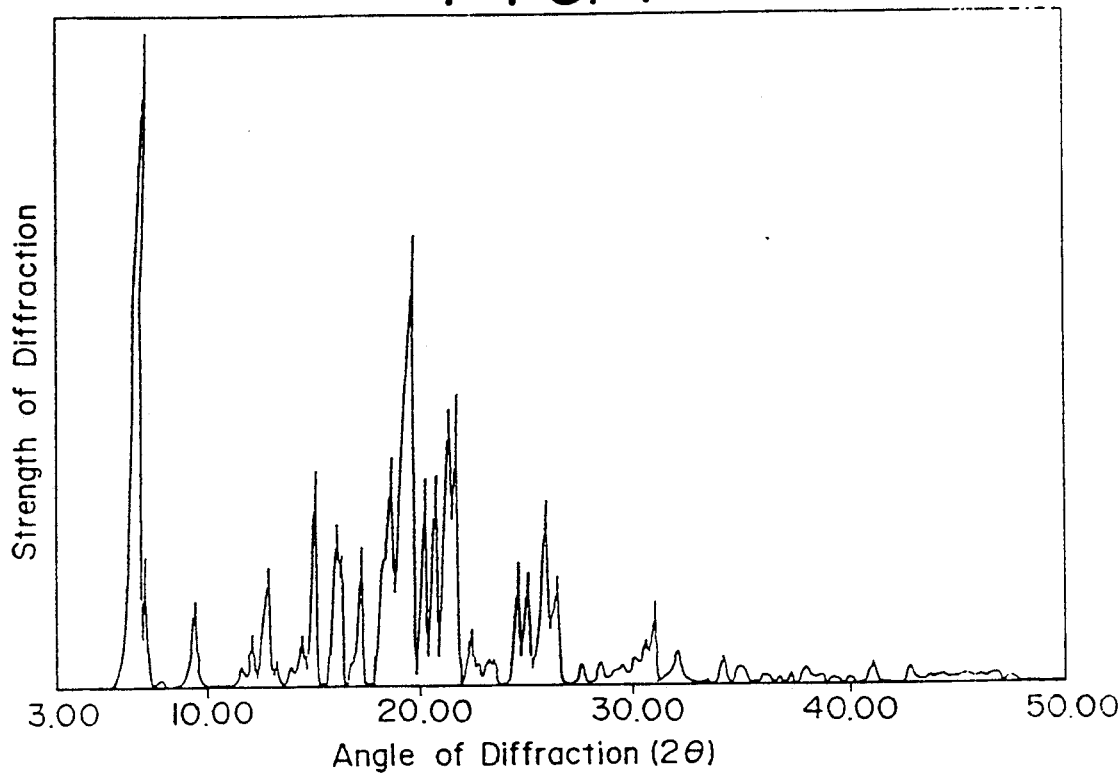
FIG. 1 is a X ray diffraction diagram of a crystal of the fluoran compound of the formula (I) which was prepared and isolated in Example 1.

In each drawing, the axis of abscissa indicates an angle of diffraction ($2\theta$) and the axis of ordinate indicates strength of diffraction.

DETAILED DESCRIPTION OF THE INVENTION

The fluoran compound represented by the formula (I) can be prepared by reacting a benzoic acid derivative of the formula (II) with a diphenylamine derivative represented by the formula (III):

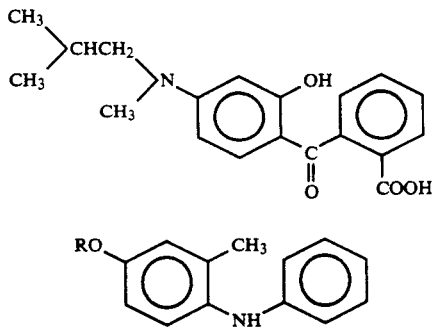

wherein R is a lower alkyl group having from 1 to 4 carbon atoms, in the presence of a dehydrating condensation agent, for example, concentrated sulfuric acid, mixture of oleum and concentrated sulfuric acid, polyphosphoric acid, phosphorus pentoxide and anhydrous aluminum chloride, preferably concentrated sulfuric acid, and thereafter bringing the reaction mixture to an alkaline pH.

The time and temperature of the dehydrating condensation reaction is not critical and is usually carried out at 0° to 100° C. for from several hours to 100 hours.

When the reaction is carried out in concentrated sulfuric acid, the preferred reaction temperature is in the range of 0° to 50° C. The reaction time depends upon the selected reaction temperature and .--. hence the reaction is conducted for a sufficient time to permit the reaction to go to completion.

After the dehydrating condensation reaction is completed, the alkali treatment is usually carried out by addition of a base, e.g., aqueous potassium hydroxide or sodium hydroxide solution to adjust the pH to an alkaline value, e.g., 9 to 12. The treatment can be conducted in a temperature range of 0° to 100° C. The alkali treatment may be conducted in the presence of an organic solvent other than water, for example, benzene or toluene.

The reaction product thus obtained is precipitated in the form of a crystal from aromatic hydrocarbon solvents such as benzene, toluene and xylene, alcohol solvents such as methanol, ethanol, isopropanol and n-butanol, polar solvents such as acetonitrile and dimethylformamide or a mixture of these solvents. The crystal of the fluoran compound of the invention can be successively isolated in the form of a stable crystal.

Alcohol solvents or polar solvents, in particular, may be used as a solvent mixture with water. In these cases, water content in the solvent mixture is preferably 50% by weight or less, more preferably 30% by weight or less, and most preferably 10% by weight or less. When the water content exceeds 50% by weight, it becomes difficult to isolate the stable crystal.

The crystal is usually precipitated by cooling the solution obtained by completely dissolving the fluoran compound in the solvent. If desired, the fluoran compound may be completely dissolved by heating to a temperature range of from room temperature to the boiling point of the solvent. After complete dissolution, the crystal is precipitated with stirring or on standing.

No particular method is required for isolation of the precipitated crystal. Conventionally known methods such as filtration can be suitably carried out.

After isolation, the crystal may be washed with an organic solvent, for example, the above solvent containing 50% by weight or less of water, or may be dissolved again in the same solvent and precipitated in the form of the crystal.

Thus obtained crystal is dried by a usual method to obtain the crystalline fluoran compound.

In preparing the compound of the formula (I), a dehydrating condensation reaction of the compound of the formula (II) with the compound of the formula (III) is carried out in the presence of a dehydrating condensation agent such as concentrated sulfuric acid and successively alkali treatment is carried out by an aqueous alkaline solution in the presence of a substantially water-insoluble organic solvent such as benzene or toluene. The compound of the formula (I) thus formed is dissolved in the organic solvent. Consequently, in the case of Conducting the alkali treatment, the crystal of the fluoran compound of the formula (I) can be suitably isolated by separating the layer of the organic solvent from the aqueous layer and successively precipitating the crystal of the fluoran compound from the solution of organic solvent.

The fluoran compounds having similar structure to the formula (I) have been known to have a different crystalline form, that is, so-called crystal modification as described in, for example, Japanese Laid-Open Patent SHO 60-202155(1985) and 62-167086(1987).

The term "crystal of the fluoran compound of the formula (I) of the invention" includes crystal modification which can exist in the fluoran compound of the formula (I) in the invention.

The crystal of the fluoran compound of the formula (I) which is suitably isolated by the above method exhibits in the powder X-ray diffraction diagram high peak at the diffraction angle ($2\theta$) of 6.9° and relatively high peak at 19.4° as illustrated in FIG. 1. (Errors of about ±0.2° can be permitted in the indication of diffraction angle.)

Figure 2:
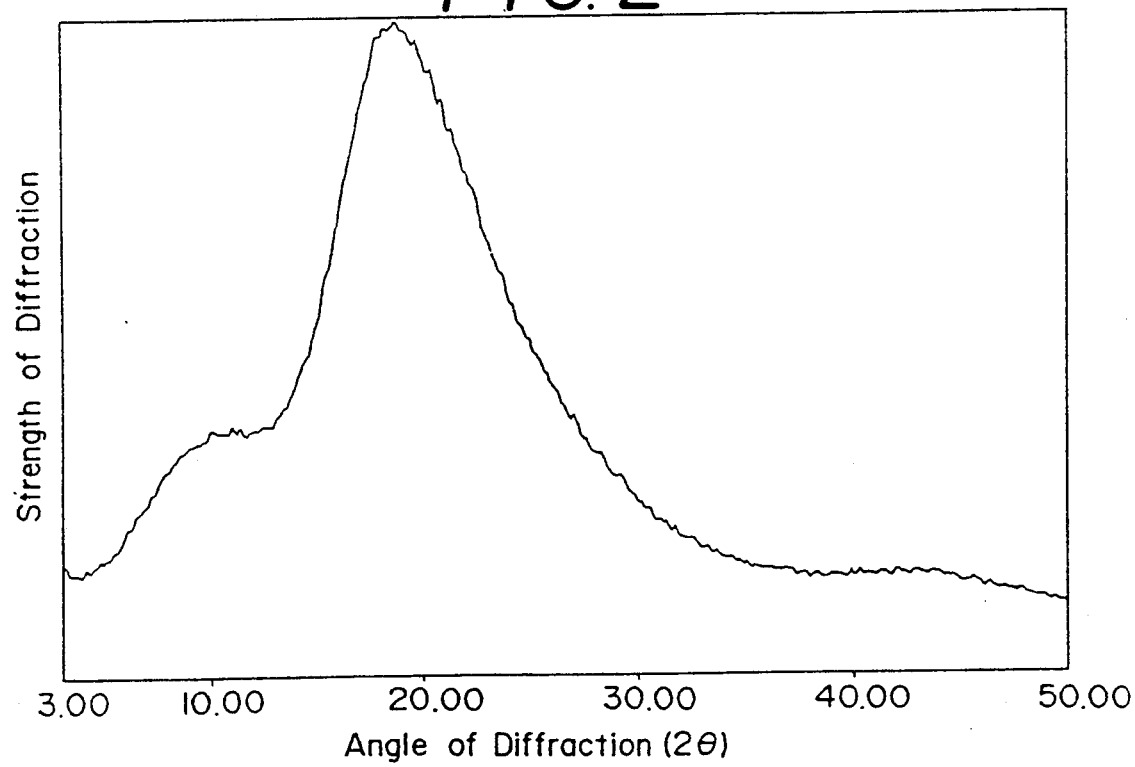
FIG. 2 is a X-ray diffraction diagram of a fluoran compound of the formula (I) which was prepared and isolated in Comparative Example 1, and had a melting point of 101° to 103° C.

The compound of the formula (I) isolated by the method disclosed in Japanese Laid Open Patent SHO 60-47066(1985) exhibits the powder X ray diffraction diagram illustrated in FIG. 2. FIG. 2 indicated substantially amorphous substance having a low degree of crystallinity.

This is, the crystal of the invention remarkably differs from that disclosed in Japanese Laid Open patent SHO 60-47066.

The crystal of the fluoran compound of the invention has a melting point of from 159° to 161° C. On the other hand, the melting point of the fluoran compound disclosed in Japanese Laid-Open Patent SHO 60-47066 has a melting point of from 101° to 103° C. Consequently, the melting point of the crystal obtained by the present invention is more than 50° C. higher than the melting point of the fluoran compound obtained by known methods.

Further, the crystal of the invention can also be prepared with ease from the above amorphous compound of the formula (I).

That is, the amorphous compound of the formula (I) is dissolved in an organic solvent having water content of 50% by weight or less, preferably 10% by weight or less. Thereafter the compound is precipitated in the form of a crystal and isolated to prepare the crystal of the invention.

The above isolated crystal of the fluoran compound of the formula (I) can be used as a color forming compound for various recording materials.

The recording materials of the present invention include pressure-sensitive recording material and heat-sensitive recording material. The crystal of the present invention is particularly suitable for use in the color forming compound of the heat-sensitive recording materials.

In such case, the fluoran compound can be used singly or as a mixture with other color forming compounds such as triphenylmethane, lactones, fluorans and spiropyrans in order to adjust the developed hue, if desired.

When preparing pressure sensitive recording material, the crystal of the invention is dissolved in the selected solvent or a mixture of the solvent. Exemplary solvents which are commonly used in the field include alkylbenzenes such as n-dodecylbenzene, alkylbiphenols such as triethylbiphenyl and diisopropylbiphenyl, hydrogenated terphenyls, alkylnaphthalenes such as dii sopropylnaphthalene, diarylethanes such as phenylxylylethane and styrenated ethylbenzene, and chlorinated paraffins. The resulting solution is sealed by a coacervation method or an interfacial polymerization method into micro capsules having an external wall comprised of gelatin, melamine-aldehyde resin, urea-aldehyde resin, polyurethane, polyurea and polyamide or the like. Aqueous dispersion of the micro-capsules is mixed with a suitable binder, such as starch and latex, and applied to a suitable substrate such as paper, plastic sheet or resin coated paper. The coated back sheet for pressure-sensitive recording is thus obtained.

The capsule dispersion can, of course, be used for a so-called middle sheet by applying the above capsule dispersion to one side of a substrate and applying a coating liquid primarily containing a developer to the other side of the substrate. A so called self contained sheets can also be prepared by applying a coating liquid containing both the above capsule and the developer to one side of a substrate, or by applying a coating liquid of the capsule to a substrate and successively applying a coating liquid of the developer on the coated layer of capsule to exist the above capsule and the developer on the same side of the substrate.

Exemplary developers suitable for use in pressure-sensitive recording material include copolymers of salicylic acid, phenols and aldehydes, for example, formaldehyde resin; alkyl, aryl or aralkyl substituted salicylic acid such as 3,5-di-α-methylbenzylsalicylic acid: polycondensate of substituted salicylic acid and styrene; alkylphenols such as octylphenol; phenol aldehyde resin such as p-phenylphenol novolak resin; metal salts of these compounds such as zinc, magnesium, aluminium, calcium, tin and nickel salts; and activated clays.

When preparing a heat-sensitive recording material of the invention, the crystal of the fluoran compound of the formula (I) and the developer are pulverized in water to form an aqueous dispersion. The fine particle dispersion thus obtained is then mixed with a binder and a filler.

Representative examples of the developer which are suitable for use in the heat sensitive recording material include bisphenol A, halogenated bisphenol A, alkylated bisphenol A, dihydroxydiphenyl sulfone, halogenated dihydroxydiphenyl sulfone, alkylated dihydroxydiphenyl sulfone, hydroxybenzoic acid esters, hydroquinone monoethers and other phenol derivatives; salicylic acid derivatives, salicylamide derivatives, urea derivatives, thiourea derivatives and other organic developers; and acid clay, attapulgite, activated clay, aluminum chloride, zinc bromide and other inorganic developers.

Exemplary binder used for the heat-sensitive recording material includes polyvinyl alcohol, modified polyvinyl alcohol, methylcellulose, hydroxyethylcellulose, carboxymethylcellulose, gum arabic, salt of styrene-maleic anhydride copolymer, and isobutylene acrylic acid-maleic anhydride copolymer. Exemplary fillers which can be used include talc, kaolin and calcium carbonate.

Other additives can also be employed, if necessary. Exemplary additives include sensitizers such as higher fatty acid amides, aromatic carboxylic acid esters, aromatic sulfonic acid esters, aromatic ethers, aromatic substituted aliphatic hydrocarbons ethers, aromatic hydrocarbons, aromatic substituted aliphatic hydrocarbons and other generally known sensitizers for the heat-sensitive recording material; UV-absorbers and defoaming agents.

The coating liquid obtained by the addition of the above additives can be applied to a suitable substrate such as paper, plastic sheet and resin coated paper, and used as the heat-sensitive recording material. The heat-sensitive recording system of the invention can of course be used in a solvent system without any problem in place of the above aqueous dispersion system. The system of the invention can also be employed for other end use applications using color forming materials, for example, a temperature-indicating material.

In the pressure-sensitive recording material, the crystal of the present invention gives high solubility in capsule oil and excellent weatherability of developed image which are important characteristics strongly desired for the color forming compound of the pressure-sensitive recording material.

Solubility of the crystal of the present invention in marketed capsule oil was compared with the solubility of the fluoran compounds of the formulas (A), (B) and (C), respectively. Results are illustrated in Table 1.

In the test, 5 parts by weight of each compound were respectively dissolved by heating in 100 parts by weight of each capsule oil. The solutions obtained were allowed to stand at 5° C. for a week. Thereafter existence of precipitated crystal was observed.

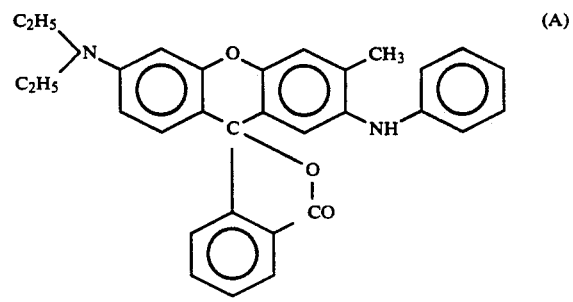

[Japanese Patent Publication SHO 48-43296 (1973)]

-continued

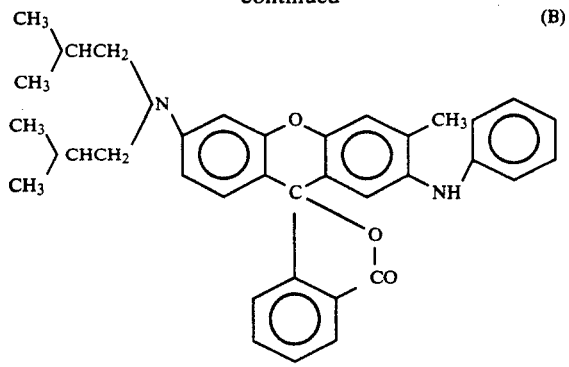

[Japanese Laid-Open Patent SHO 61-264058 (1986)] (B)

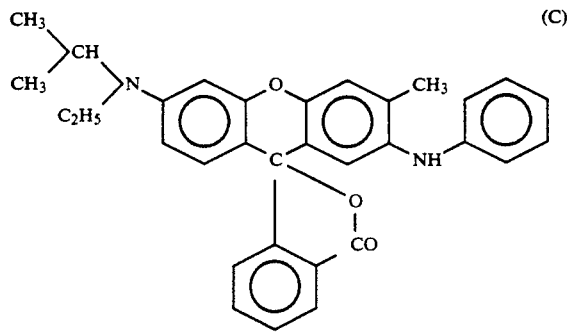

[Japanese Laid-Open Patent SHO 60-47068 (1985)] (C)

TABLE 1

| Capsule oil | SAS - 296 | KMC - 113 |
|---|---|---|
| Crystal of the Invention | ◯ | ◯ |
| Compound of the formula (A) | X | X |
| Compound of the formula (B) | X | X |
| Compound of the formula (C) | X | X |

In Table 1, ◯ means that no crystals are precipitated and X means that precipitation of crystals is observed.

SAS-296 is a capsule oil produced by Nippon Petrochemical Co., and KMC-113 is a capsule oil produced by Kureha Chemical Co.

As clearly illustrated in Table 1, the crystal of the present invention has higher solubility in each capsule oil, in constradistinction to the fluoran compounds of the formulas (A), (B) and (C).

These results means that crystal precipitation does not occur during storage in capsule oil in the preparation of the pressure-sensitive recording material, and further that crystal precipitation in the microcapsules is not liable to occur after preparation of the microcapsules. The property is a remarkable characteristic of the crystal of the present invention.

The heat-sensitive recording material prepared by using the crystal of the present invention has extremely excellent properties as compared with the recording material obtained by using the compound of the formula (I) which is prepared by the process disclosed in Japanese Laid-Open Patent SHO 60-47066(1985) and has a melting-point of 101° to 103° C., or by using the known compound of the formula (D). For example, when bisphenol A is used as a developer, the heat resistant recording paper obtained by the process of the invention is very excellent in whiteness (brightness) of paper immediately after application of the coating liquid and in storage stability, i.e., resistance to light, moisture and heat, of uncolored portion of the coated paper, as illustrated in Table 2.

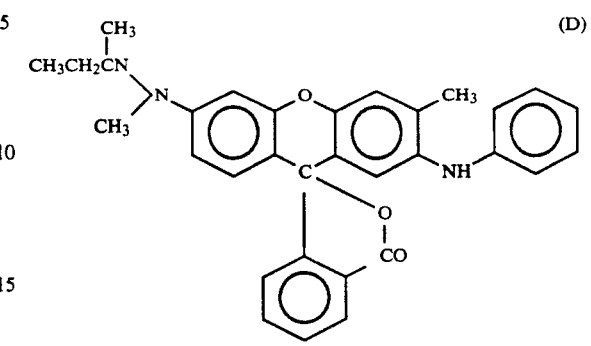

[Japanese Laid-Open Patent SHO 60-47068 (1985)] (D)

TABLE 2

| Compound | Immediately after application | Light resistance | Moisture and heat resistance |
|---|---|---|---|
| Crystal of the invention | ◯ | ◯ | ◯ |
| Fluoran compound of m.p. 101–103° C. | X | X | X |
| Compound of formula (D) | X | X | X |

Results were evaluated by visual observation. Evaluation at immediately after application was conducted by observing the brightness of the paper.

◯ ... High brightness

X ... Soiled to dark gray

Evaluation of light resistance was conducted by inspecting the degree of yellowing in the uncolored portion after exposure to sun-light for 10 hours.

◯ ... Almost no yellowing and maintain high brightness

X ... Remarkable yellowing or discolored to yellow brown.

Evaluation of moisture and heat resistance was conducted by examining the soiling of the uncolored portion after storage at 60° C. for 24 hours in 90% relative humidity.

◯ ... Almost no soiling and high brightness

X ... Remarkably soiled to dark gray

Further, the heat-sensitive recording material prepared by using the crystal of the present invention provides a developed image having very excellent storage stability. For example, when bisphenol A is used as a developer, the heat-sensitive recording paper prepared by using the crystal of the present invention as a color forming compound provides a developed image having very excellent water resistance as compared with the image obtained by using the compound of the formula (E) as illustrated in Table 3.

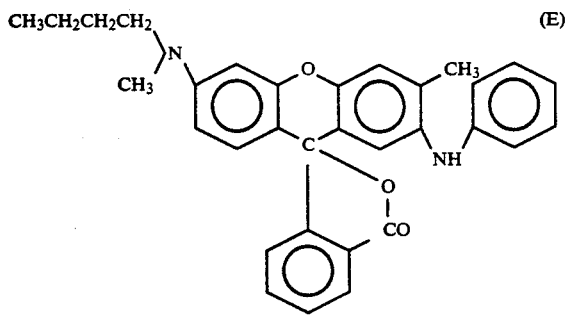

[Japanese Laid-Open Patent SHO 59-68373 (1984)]

The water resistance test was carried out by using the heat-sensitive recording paper prepared by using each compound. The recording paper having a developed color density of 0.9 measured with a Macbeth reflection densitometer (Trade Mark; TR-524) was immersed in water at 25° C. for 24 hours.

Color density after water resistance test and residual rate are illustrated in Table 3.

$$\text{Residual rate (\%)} = \frac{\text{Color density after test}}{\text{Color density before test (0.9)}} \times 100$$

TABLE 3

| Compound | Color density after test | Residual rate (%) |
| --- | --- | --- |
| Crystal of the invention | 0.65 | 72 |
| Compound of formula (E) | 0.14 | 16 |

As clearly seen in Table 3, the heat-sensitive recording paper prepared by using the compound of the formula (E) developed image having poor water resistance. By visual inspection, the image had been almost disappeared after the water resistance test.

The present invention will hereinafter be illustrated further n detail by way of examples. However, it is to be understood that the invention is not intended to be limited to the specific embodiments.

EXAMPLE 1

In 720 g of 96% sulfuric acid, 107 g of 2-(4'-N-isobutyl N-methylamino-2'-hydroxybenzoyl)benzoic acid was dissolved at 10° to 15° C., and then 70 g of 4-methoxy-2-methyldiphenylamine (the compound of the formula (III) wherein R is methyl) was added at the same temperature. The mixture was stirred at 10° to 15° C. for 24 hours and poured into 4000 ml of ice water. Precipitated solid was collected, washed with water, and added to 1000 ml of a 10% aqueous sodium hydroxide solution. Further 1000 ml of toluene was added to the mixture thus obtained and stirred for 2 hours at 60° to 70° C. Toluene layer was seperated, washed with warm water until the wash water becomes neutral, and the resulting toluene layer was concentrated at 40° C. under reduced pressure. Precipitated crystal was filtered, washed with a small amount of toluene, further washed with methanol, and dried at 60° C. for 24 hours to obtain 126 9 of the fluoran compound of the formula (I) as a colorless crystal having a melting point of 159° to 161° C.

The toluene solution of the compound was colorless and transparent, and quickly developed reddish black color on silica gel.

In 95% acetic acid solution, the compound had maximum absorption at 455 nm and 594 nm.

Powder X ray diffraction diagram is illustrated in FIG. 1.

COMPARATIVE EXAMPLE 1

Preparation of the compound of the formula [I] by the process disclosed in Japanese Laid-Open Patent SHO 60 47066

In 150 g of 96% sulfuric acid, 16.4 g of 2-(4'-N-isobutyl-N-methylamino-2'-hydroxybenzoyl)benzoic acid was dissolved at 10° to 15° C., and then 10.7 g of 4-methoxy-2-methyldiphenylamine was added at the same temperature. The mixture was stirred at 10° to 15° C. for 24 hours and poured into 800 g of ice water. Precipitated solid was filtered, washed with water, and added to 800 ml of water. To the resulting mixture, 200 ml of a 10% aqueous sodium hydroxide solution was added and stirred for 2 hours at 60° to 70° C. The solid was filtered, washed with water and dried to obtain 24 g of dried product. The dried product was washed with 30 g of ethylene glycol and then dissolved in 500 g of a 60% aqueous methanol. Thereafter, solid reprecipitated from the solution was filtered and dried at 30° C. to obtain 13.5 g of white solid powder like having a melting point of 101° to 103° C.

Powder X-ray diffraction diagram is illustrated in FIG. 2.

EXAMPLE 2

Ten grams of the amorphous compound of the formula [I] prepared in Comparative Example 1 were added to 80 ml of isopropanol and dissolved at 60° C. The solution was cooled to room temperature. Precipitated crystal was filtered and dried to obtain 9 g of colorless crystal having a melting point of 159° to 161° C.

Powder X-ray diffraction diagram was the same as in Example 1.

EXAMPLE 3

Preparation of heat sensitive recording paper by using the crystal of the invention A mixture composed of 10 g of the crystal obtained in Example 1, 5 g of a 10% aqueous polyvinyl alcohol solution and 37.5 g of water was pulverized with a sand mill to a particle size of 3 μm.

Separately, bisphenol A was dispersed similarly to obtain a 38 aqueous developer dispersion. A mixture was prepared by mixing 65.8 g of the developer dispersion, 50 g of the above dispersion of the crystal, 18.3 g of a 60% aqueous dispersion of precipitated calcium carbonate, 88 g of a 10% aqueous polyvinyl alcohol solution and 51.9 g of water.

The mixture was applied to a white paper with a wire rod No. 10 and dried at room temperature to obtain heat sensitive recording paper having high brightness without soil. The heat-sensitive recording paper very quickly developed slightly reddish black color by heating.

After exposing the heat-sensitive recording paper to sunlight for 20 hours, the uncolored portion caused almost no yellowing and retained high brightness. After storing at 60° C. for 24 hours under 90% relative humidity, the uncolored portion caused no soil and retained high brightness as illustrated in Table 2.

When the heat-sensitive recording paper was developed to an image density of 0.9 and immersed into water at 25° C. for 24 hours, residual rate of the image was good as illustrated in Table 3.

COMPARATIVE EXAMPLE 2

Preparation of heat sensitive recording paper by using the fluoran compound of the formula (I) which was obtained in Comparative Example 1 and had a melting point of 101° to 103° C.

A heat-sensitive recording paper was prepared by carrying out the same procedures as described in Example 3 except that the crystal isolated in Example 1 was replaced by the compound obtained in Comparative Example 1. The paper was already soiled to dark gray immediately after coating. After exposing the recording paper to sunlight for 20 hours, remarkable yellowing was found on the uncolored portion.

After storing the recording paper at 60° C. for 24 hours under 90% relative humidity, the uncolored portion was remarkably soiled to dark gray as illustrated in Table 2.

COMPARATIVE EXAMPLE 3

Preparation of heat-sensitive recording paper by using the fluoran compound of the formula (D)

A heat-sensitive recording paper was prepared by carrying out the same procedures as described in Example 3 except that the crystal isolated in Example 1 was replaced by the fluoran compound of the formula (D). The paper was already soiled to dark gray immediately after coating. After exposing the recording paper to sunlight for 20 hours, remarkable yellowing was found on the uncolored portion.

After storing the recording paper at 60° C. for 24 hours under 90% relative humidity, the uncolored portion was remarkably soiled to dark gray as illustrated in Table 2.

COMPARATIVE EXAMPLE 4

Preparation of heat-sensitive recording paper by using the fluoran compound of the formula (E)

A heat-sensitive recording paper was prepared by carrying out the same procedures as described in Example 3 except that the crystal isolated in Example 1 was replaced by the fluoran compound of the formula (E). The recording paper was developed to image density of 0.9 and immersed into water at 25° C. for 24 hours. After immersion, the image density was remarkably decreased and the image was almost disappeared as illustrated in Table 3.

EXAMPLE 4

Preparation of pressure sensitive recording paper by using the crystal of the invention Coated back sheet (CB) and coated front sheet (CF) were prepared by the following procedures.

A mixture of 100 g of a 10% aqueous solution of ethylenemaleic anhydride copolymer and 240 g of water was adjusted to pH 4.0 with a 10% aqueous sodium hydroxide solution and mixed with 200 g of a solution containing 5% by weight of the crystal obtained in Example 1 in phenylxylylethane (SAS-296;Trade Mark of Nippon petrochemical Co.). Afters emulsifying the resultant mixture with a homomixer, 60 g of an aqueous methylolmelamine solution containing 50% of solid (Uramine T-30; Trade Mark of a product of Mitsui Toatsu Chemicals Inc.) was added, and stirred at 55° C. for 3 hours to obtain a microcapsule dispersion having an average particle size of 5.0 μm.

To 100 g of the microcapsule dispersion, 40 g of wheat starch particle, 20 g of a 20% paste of oxidized starch and 116 g of water were added and dispersed.

The dispersion thus obtained was applied on a paper having a basis weight of 40 g/m² so as to obtain a coating weight of 5 g/m² as solid. CB sheet was thus obtained.

On the other hand, CF sheet was prepared by using zinc salt of substituted salicylic acid styrene copolymer as a developer. The zinc salt was pulverized in water with a sand grinding mill in the presence of a small amount of a high molecular weight anionic surfactant to obtain an aqueous dispersion with a 40% by weight of solids content.

Using the aqueous dispersion, a coating compound (30% solid content) having the below described composition was prepared and applied on a woodfree paper having a basis weight of 40 g/m² so as to obtain a coating weight of 5.5 g/m² after drying. A CF sheet was thus obtained.

| Aqueous Coating Composition | Weight of solid (g) |
|---|---|
| Precipitated calcium carbonate | 100 |
| Developer | 20 |
| Binder | |
| (Oxidized starch) | 8 |
| (Synthetic latex) | 8 |

The microcapsule coated CB sheet and the developer coated CF sheet were overlapped so as to bring both coated surfaces into contact with each other.

When pressure was applied on the overlapped sheets with a pencil, a reddish black image emerged on the developer coated surface. The developed color image had no problem on resistance to light, moisture and NOx in practical use.

What is claimed is:

1. A process for preparing the crystalline form of the fluoran compound having the formula (I):

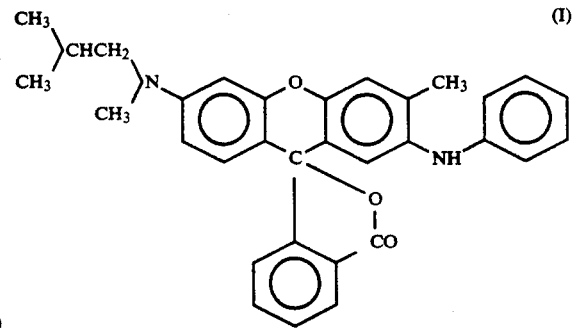

which has a melting point of from 159° to 161° C. and an X-ray diffraction diagram by Cu-Kα beams which indicates a high peak at a diffraction angle 2θ of 6.9° and a relatively high peak at 19.4°, comprising precipitating the fluoran compound of the formula I in crystalline form from an organic solvent solution containing said fluoran compound and having a water content of 50% by weight or less, and isolating the thus-precipitated crystalline form.

2. The process of claim 1 wherein the fluoran compound in the organic solvent having a water content of 50% by weight or less is obtained by conducting a dehydrating condensation reaction of the compound having the formula (II) with a compound having the formula (III):

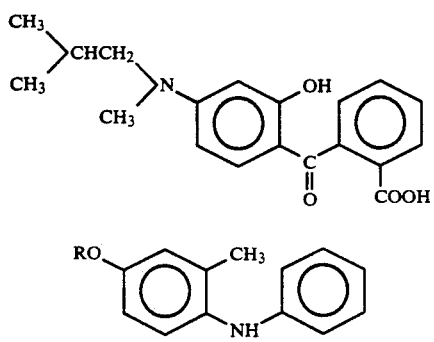

wherein R is lower alkyl of from 1 to 4 carbon atoms, and a subsequent alkali treatment in the presence of the organic solvent.

3. A process for preparing the crystalline form of the fluoran compound having the formula (I):

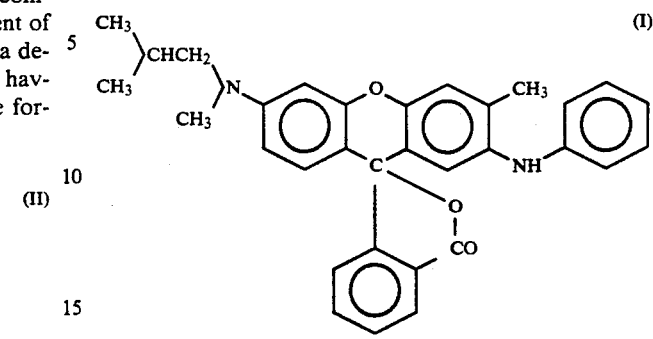

which has a melting point of from 159° to 161° C. and an X-ray diffraction diagram by Cu-Kα beams which indicates a high peak at a diffraction angle $2\theta$ of 6.9° and a relatively high peak at 19.4°, comprising dissolving an amorphous form of the fluoran compound in an organic solvent having a water content of 50% by weight or less, precipitating said compound in crystalline form and isolating the thus-precipitated crystalline form of said compound.

* * * * *